United States Patent
Kühn et al.

(10) Patent No.: US 7,569,621 B2
(45) Date of Patent: *Aug. 4, 2009

(54) DYED POLYMETHYL METHACRYLATE BONE CEMENT AND PROCESS FOR ITS PRODUCTION

(75) Inventors: Klaus-Dieter Kühn, Marburg (DE); Sebastian Vogt, Erfurt (DE)

(73) Assignee: Heraeus Kulzer GmbH, Hanau (DE)

( * ) Notice: Subject to any disclaimer, the term of this patent is extended or adjusted under 35 U.S.C. 154(b) by 95 days.

This patent is subject to a terminal disclaimer.

(21) Appl. No.: 11/483,339

(22) Filed: Jul. 7, 2006

(65) Prior Publication Data

US 2007/0031469 A1    Feb. 8, 2007

(30) Foreign Application Priority Data

Jul. 7, 2005    (DE) .................. 10 2005 032 110

(51) Int. Cl.
    *A61F 2/28*    (2006.01)
(52) U.S. Cl. .................. 523/115; 523/112; 523/117
(58) Field of Classification Search .................. 523/117, 523/112, 115
    See application file for complete search history.

(56) References Cited

U.S. PATENT DOCUMENTS

| | | | | |
|---|---|---|---|---|
| 4,373,217 A | * | 2/1983 | Draenert | 623/23.62 |
| 4,588,583 A | * | 5/1986 | Pietsch et al. | 523/116 |
| 5,258,420 A | * | 11/1993 | Posey-Dowty et al. | 523/116 |
| 6,680,308 B1 | * | 1/2004 | Hassan | 514/125 |
| 6,743,438 B2 | * | 6/2004 | Thakrar et al. | 424/427 |
| 2006/0062825 A1 | * | 3/2006 | Maccecchini | 424/423 |
| 2006/0293407 A1 | * | 12/2006 | Kuhn et al. | 523/116 |

* cited by examiner

*Primary Examiner*—Tae H Yoon
(74) *Attorney, Agent, or Firm*—Norris McLaughlin & Marcus

(57) ABSTRACT

A dyed polymethyl methacrylate bone cement is described which is characterized by at least the surface of the polymer particles of the powder component being coated partially or completely with a mixture of one or several dyes and a hydrophobic, low molecular or oligomeric organic coupling agent, such a quantity of coupling agent being present that the polymer particles can be visually recognized as not having swollen.

13 Claims, No Drawings

DYED POLYMETHYL METHACRYLATE BONE CEMENT AND PROCESS FOR ITS PRODUCTION

The subject matter of the invention is a dyed polymethyl methacrylate bone cement.

BACKGROUND OF THE INVENTION

Polymethyl methacrylate bone cements (PMMA bone cements) have been widely used in the field of medicine for decades for anchoring endoprostheses in the bone (Klaus-Dieter Kühn: Knochenzemente für die Endoprothetik: ein aktueller Vergleich der physikalischen und chemischen Eigenschaften handelsüblicher PMMA-Zemente (Bone cements for endoprosthetics: a current comparison of the physical and chemical properties of commercial PMMA cements). Springer Verlag Berlin Heidelberg New York, 2001). Polymethyl methacrylate bone cements consist in general of a liquid monomer component and a powder component. The liquid monomer component consists of methyl methacrylate and an activator. N,N-Dimethyl-p-toluidine is preferably used as the activator. As a rule, the powder component consists of polymethyl methacrylate or polymethyl methacrylate co-methyl acrylate, an x-ray contrast agent and a radical initiator. Zirconium dioxide and barium sulphate are commonly used as x-ray contrast agents. Dibenzoyl peroxide is preferably used as radical initiator. After mixing the monomer component and the powder component, the bone cement is hardened by radical polymerisation of the monomer within a few minutes.

After mixing, common polymethyl methacrylate bone cements are present as a white to slightly yellowish paste-like mass. As a result, an optical differentiation between the bone cement and the bone tissue causes problems from time to time when the mixed bone cement is introduced into the bone. However, it is desirable for the bone cement to be visually distinguishable without problems from the surrounding bone tissue.

For this reason, the polymethyl methacrylate bone cements which have been produced by Heraeus Kulzer GmbH for approximately 30 years have a green colour. This colour is achieved by way of a green monomer component and a green powder component. Chlorophyllin is contained as dye in both components.

In the case of the polymethyl methacrylate bone cements from Heraeus Kulzer GmbH, the chlorophyllin is dissolved in the liquid monomer component by means of refined peanut oil (Biskin®) as solubiliser. Apart from the dyed monomer components, polymethyl methacrylate bone cements can also contain a dyed powder component. A method, known as such, for dyeing the powder component of the polymethyl methacrylate bone cements consists of using dyed polymethyl methacrylate particles or polymethyl methacrylate co-methyl acrylate particles. These can be combined with a non-dyed second polymer in order to influence the characteristics of the polymethyl methacrylate bone cements. One of the problems occurring in this case involves accurately reproducing the colour, the colour impression of the powder component even in the case of different mixing ratios of the dyed polymer to the non-dyed polymer.

The synthesis of dyed polymethyl methacrylate particles or polymethyl methacrylate co-methyl acrylate particles in the course of which the dye is enclosed, during bead polymerisation, in the polymer beads being formed is highly complex and labour/time consuming under industrial conditions. A major reason for this is the occasionally low stability of dyes vis-à-vis the radical initiators used in bead polymerisation and vis-à-vis the radicals occurring during polymerisation. The initiators, in particular, can cause oxidation processes and consequently decolourise the dye.

The consistent nature of the polymethyl methacrylate bone cements, in terms of colour, is an essential factor for the acceptance of the bone cements by the customer and consequently of economic importance.

SUMMARY OF THE INVENTION

The invention is consequently based on the object of developing a dyed polymethyl methacrylate bone cement which overcomes the known problems of the polymethyl methacrylate bone cements previously commonly used. The powder component of the polymethyl methacrylate bone cement should be such that the colour can be reproduced reliably. It should be possible to use cheap undyed polymers such as polymethyl methacrylate or polymethyl methacrylate co-methyl acrylate or polymethyl methacrylate costyrene and copolymers or terpolymers of similar composition for the production of dyed polymethyl methacrylate bone cements. In this connection, it is important that the colour impression of the bone cement in the powder component is uniform. This means that the colour of the powder component must be recognisable visually as being homogeneous. In addition, it is important that the powder component of the polymethyl methacrylate bone cement in terms of its flowability does not differ from the flowability and the swelling behaviour of undyed polymethyl methacrylate bone cements.

The object has been achieved according to the invention by a dyed polymethyl methacrylate bone cement in the case of which at least the surface of the polymer particles of the powder component has been coated partially or completely with a mixture of one or several dyes and a hydrophobic, low molecular or oligomeric organic coupling agent, such a quantity of coupling agent being present that the polymer particles can be visually recognised as not having swollen. By using a hydrophobic coupling agent, it is possible to apply small quantities of dye evenly onto the polymer particles in such a way that these adhere firmly on the polymer particles. In this way, the dye or the dyes are fixed on the particle surface. It is important in this connection that only small quantities of coupling agent are present. Larger quantities of coupling agent might cause the polymer particles to partially swell or partially dissolve, thus caking them together. The flowability and consequently also the swellability of the powder component would thus change considerably compared with an undyed polymethyl methacrylate bone cement.

DETAILED DESCRIPTION

If necessary, the surface of the x-ray contrast agent barium sulphate and/or zirconium oxide or, if necessary, the surface of all the components of the powder component can be coated partially or completely with a mixture of one or several dyes and a hydrophobic, low molecular or oligomeric organic coupling agent. Preferably, the dye or dyes are soluble or suspended in the hydrophobic, low molecular or oligomeric organic coupling agent. Thus, chlorophyllin (E141), for example, dissolves in Biskin or oleic acid ethyl ester. The term "suspended" should be understood to mean that the dye particles have a grain size of less than/equal to 1 µm and are homogenously distributed in the coupling agent.

Moreover, oleic acid esters and/or elaidic acid esters and/or linoleic acid esters and/or linolenic acid esters of aliphatic alcohols with 1 to 22 carbon atoms or oligomers of these esters are preferred as coupling agents.

Moreover, methacrylic acid esters or acrylic acid esters of aliphatic alcohols with 4 to 16 carbon atoms or oligomers of these methacrylic acid esters or acrylic acid esters with a molecular weight of less than 3,000 g/mole are preferred as coupling agents. It is also possible to use oligomers of this structure with molecular weights of more than 3,000 g/mole as coupling agents provided these are paste-like or viscous at room temperature.

Oleic acid, elaidic acid, linolenic acid, glycerine trioleate, glycerine elaidinate, glycerine trilinolenate, ethylene glycol dioleinate, ethylene glycol dielaidinate, ethylene glycol trilinolenate and their oligomers are particularly preferred as coupling agents. These oligomers can be produced by the action of air at elevated temperatures, as so-called blown oils, or by heating in the absence of atmospheric oxygen as so-called stand oils. It is also possible to use mixed esters of glycerine, of ethylene glycol, of sorbitol, of mannitol, of xylitol, of erythrols, of 1,1,1-trimethylol propane with the unsaturated fatty acids oleic acid, elaidic acid, linolenic acid and arachidonic acid and the oligomers derived therefrom as coupling agents.

Preferably, coupling agents are used in one embodiment which are produced synthetically or partially synthetically and which contain no proteins or decomposition products of proteins. This characteristic is particularly important because the risk of allergies occurring is minimised when protein-free coupling agents are used.

However, refined peanut oil, hardened linseed oil, hardened rapeseed oil and sunflower oil can also be used as coupling agents. The use of further fats and vegetable oils commonly used in the human diet is also possible.

Appropriately, the coupling agent should contain free radical polymerisable double bonds. In this way, the coupling agent can take part in the polymerisation during curing of the bone cement and is firmly integrated into the bone cement.

Moreover, it is appropriate that mixtures of the coupling agent and the dye or the dyes in methyl methacrylate or mixtures of methyl methacrylate are soluble with other methacrylic acid esters such as methacrylic acid ethyl ester, methacrylic acid isobornyl ester and methacrylic acid 2-ethyl hexyl ester and acrylic acid esters such as acrylic acid methyl ester. On mixing of the powder components with the liquid monomer component, the mixture of the dye or the dyes and the coupling agent can dissolve in the liquid monomer component and dye this as well. This means that the coating is removed at least partially by the action of the monomer and forms a solution with the monomer. In this way, a uniform colour impression of the polymethyl methacrylate bone cement is achieved during curing because the free radical polymerising monomer contains the dye in the dissolved state and consequently polymerises during curing to form a polymer appearing coloured.

Particularly preferred dyes are chlorophyll, chlorophyllin (E141), indigo, malachite green, crystal violet, brilliant blue, brilliant green, copper phthalocyanin, cobalt phthalocyanin, carotene, vitamin B12 and derivates derived therefrom.

A process according to the invention for dyeing the powder component described above consists essentially of the polymer particles or mixtures of polymer particles and the x-ray contrast agent or mixtures of the polymer particles, the x-ray contrast agent and the initiator being coated with a liquid or paste-type mixture of the dye or the dyes and the coupling agent by mixing in a temperature range of 0° C. to 50° C. in the presence of air or inert gas in such a way that the layer thickness of the mixture on the coated particles is less than 2 µm and that the coated particles are not caked together. In this respect, it is particularly advantageous if the mixing process is carried out in such a way that the glass transition point of the polymer particles is not exceeded. Exceeding the glass transition point leads to caking of the polymer particles and consequently the formation of agglomerates. The mixing process can advantageously be carried out in mixers commonly used in industry, such as mechanically agitated mixers or Röhn wheel mixers. Advantageously, the coating operation can be carried out at temperatures around 40° C. because the viscosity of the heated coupling agent is lower than the viscosity of the coupling agent at room temperature. Consequently, a uniform distribution of the coupling agent is more easily possible.

The invention will now be explained by the following examples without restricting the invention.

EXAMPLE 1

In a plastic bottle with a screw closure, 33.2 g of a polymethyl methacrylate co-methyl acrylate (molecular weight ~600,000 g/mole, particle size 4-50 µm) are mixed with 4.0 mg of a mixture in the case of which 1.0 mg of chlorophyll are dissolved in 3.0 mg of oleic acid ethyl ester, in a Turbula tumble mixer for 24 hours at room temperature. After 24 hours, the previously colourless polymer has acquired a greenish coloration. The polymer particles have not swollen and not caked together. Subsequently, 6.3 g of zirconium dioxide and 0.84 g of dibenzoyl peroxide (desensitised with 25% water) are added to the dyed polymer and mixing is carried out for 10 minutes at room temperature by means of the Turbula tumble mixer. The free-flowing mixture formed which visually appears to be homogeneous is used as powder component of a polymethyl methacrylate bone cement.

EXAMPLE 2

In a plastic bottle with a screw closure, 33.2 g of a polymethyl methacrylate co-methyl acrylate (molecular weight ~600,000 g/mole, particle size 5-40 µm) and 6.3 g of zirconium dioxide are mixed with 3.0 mg of a mixture in the case of which 1.0 mg of chlorophyll is dissolved in 2.0 mg of oleic acid ethyl ester, in a Turbula tumble mixer for 24 hours at room temperature. After 24 hours, the previously colourless polymer has cquired a greenish coloration. Subsequently, 0.84 g of dibenzoyl peroxide (desensitised with 25% water) are added to the dyed mixture and mixed for 10 minutes at room temperature by means of the Turbula tumble mixer. The mixture formed which visually appears to be homogeneous is used as the powder component of a polymethyl methacrylate bone cement.

EXAMPLE 3

The powder component of a polymethyl methacrylate bone cement is produced in a manner analogous to example 1, although 4.0 mg of a mixture consisting of 1.0 mg of chlorophyll and 3.0 mg of glycerine trioleinate is used.

EXAMPLE 4

The powder component of a polymethyl methacrylate bone cement is produced in a manner analogous to example 1, although 4.0 mg of a mixture consisting of 1.0 mg of brilliant blue and 3.0 mg oleic acid are used.

EXAMPLE 5

A liquid monomer component is produced from 18.40 g of methyl methacrylate and 0.38 g of N,N-dimethyl-p-toluidine by mixing. This mixture represents the monomer component of the following cements.

39.00 g of the powder component of examples 1-4 are combined with 18.00 g of the monomer component respectively. On mixing of the powder component with the liquid monomer component, a green paste capable of plastic deformation is formed at room temperature after 1 minute. This remains processable for 3 minutes and then hardens. A green solid is formed.

EXAMPLE 6

A liquid monomer component is produced by mixing 18.40 g of methyl methacrylate, 0.38 g of N,N-dimethyl-p-toluidine and 1.0 mg of chlorophyll which is dissolved in 2.0 mg oleic acid ethyl ester. This green mixture represents the monomer component of the following cements.

39.00 g of the powder component of examples 1-4 are combined with 18.00 g of the monomer component respectively. On mixing of the powder component with the liquid monomer component, a green paste capable of plastic deformation is formed at room temperature after 1 minute. This remains processable for 3 minutes and then hardens to form a green solid.

We claim:

1. Dyed polymethyl methacrylate bone cement comprised of a liquid and a powder component, wherein the powder component is comprised of polymer particles and the polymer particles have a surface, and wherein the surface of the polymer particles of the powder component is partially or completely coated with a mixture of one or several dyes and a hydrophobic low molecular or oligomeric organic coupling agent, the amount of coupling agent being an amount that will result in the polymer particles are being recognizable as not having swollen.

2. Dyed polymethyl methacrylate bone cement according to claim 1 wherein the powder component further comprises barium sulphate and/or zirconium oxide and the barium sulphate and/or zirconium oxide have a surface and the surface of the barium sulphate and/or zirconium oxide or the surfaces of all the components of the powder component are also partially or completely coated with a mixture of one or several dyes and a hydrophobic low molecular or oligomeric organic coupling agent.

3. Dyed polymethyl methacrylate bone cement according to claim 1, wherein the dye or dyes are dissolved or suspended in the hydrophobic, low molecular or oligomeric organic coupling agent.

4. Dyed polymethyl methacrylate bone cement according to claim 1, wherein the dye/dyes to hydrophobic, low molecular or oligomeric organic coupling agent has a mass ration of 1.0:0.1 to 1.0:10.0.

5. Dyed polymethyl methacrylate bone cement according to claim 1, wherein said coupling agent is selected from the group consisting of oleic esters, and/or elaidic acid esters, linoleic acid esters, linolenic acid esters of aliphatic alcohols with 1 to 22 carbon atoms and oligomers of said esters.

6. Dyed polymethyl methacrylate bone cement according to claim 1, wherein said coupling agent is selected from the group consisting of methacrylic acid esters or acrylic acid esters of the aliphatic alcohols with 4 to 16 carbon atoms and oligomers of said methacrylic acid esters or acrylic acid esters with a molecular weight of less than 3,000 g/mole.

7. Dyed polymethyl methacrylate bone cement according to claim 1, wherein said coupling agent is selected from the group consisting of oleic acid, elaidic acid, linolenic acid, glycerine trioleate, glycerine elaidinate, glycerine trilinolenate, ethylene glycol dioleinate, ethylene glycol dielaidinate, ethylene glycol trilinolenate and their oligomers.

8. Dyed polymethyl methacrylate bone cement according to claim 1, wherein said coupling agents are produced synthetically or partially synthetically and do not contain proteins or decomposition products of proteins.

9. Dyed polymethyl methacrylate bone cement according to claim 1, wherein said coupling agent is selected from the group consisting of refined peanut oil, hardened linseed oil, hardened rapeseed oil and sunflower oil.

10. Dyed polymethyl methacrylate bone cement according to claim 1, wherein the coupling agent contains free radical polymerizable double bonds.

11. Dyed polymethyl methacrylate bone cement according to claim 1, wherein the mixture of coupling agent and the dye or the dyes is soluble in methyl methacrylate.

12. Dyed polymethyl methacrylate bone cement according to claim 1, wherein said dyes are selected from the group consisting of chlorophyll, chlorophyllin, indigo, malachite green, crystal violet, brilliant blue, brilliant green, copper phthalocyanin, cobalt phthalocyanin, carotene, and vitamin B12.

13. Process for dyeing the polymer particles of the powder component of polymethyl methacrylate bone cement wherein the polymer particles or mixtures of polymer particles and an x-ray contrast agent or mixtures of polymer particles, x-ray contrast agent and an initiator are coated with a liquid or paste mixture of the dye or the dyes and a coupling agent by mixing in a temperature range of 0° C. to 50° C. in the presence of air or inert gas in such a way that the layer thickness of the mixture on the coated particles is less than 2 μm and that the coated particles are not caked together.

* * * * *